(12) United States Patent
Wilson et al.

(10) Patent No.: US 6,701,168 B1
(45) Date of Patent: Mar. 2, 2004

(54) APPARATUS FOR MEASURING AN OXYGEN CONCENTRATION GRADIENT AND METHOD OF USE THEREOF

(75) Inventors: David F. Wilson, Philadelphia, PA (US); Sergei A. Vinogradov, Philadelphia, PA (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 10/111,831

(22) PCT Filed: Oct. 13, 2000

(86) PCT No.: PCT/US00/41171

§ 371 (c)(1),
(2), (4) Date: Sep. 27, 2002

(87) PCT Pub. No.: WO01/27585

PCT Pub. Date: Apr. 19, 2001

Related U.S. Application Data

(60) Provisional application No. 60/159,616, filed on Oct. 14, 1999.

(51) Int. Cl.⁷ .................................................. A61B 5/00
(52) U.S. Cl. ........................................ 600/317; 436/68
(58) Field of Search ................................. 600/310, 317, 600/322; 436/68

(56) References Cited

U.S. PATENT DOCUMENTS

| | | |
|---|---|---|
| 4,476,870 A | 10/1984 | Peterson et al. |
| 4,947,850 A | 8/1990 | Vanderkooi et al. |
| 5,186,173 A | 2/1993 | Zuckerman |
| 5,501,225 A | 3/1996 | Wilson et al. |
| 5,515,694 A | 5/1996 | Meloling et al. |
| 5,515,864 A | 5/1996 | Zuckerman |
| 5,528,356 A * | 6/1996 | Harcourt ................. 356/73.1 |
| 5,757,013 A * | 5/1998 | Groger et al. ............. 356/317 |
| 5,830,138 A | 11/1998 | Wilson |

OTHER PUBLICATIONS

R. Shrager, "Quadratic Programming for Nonlinear Regression", *Numerical Mathematics* 15:41 (1972).

Vanderkooi et al., "A New Method for Measuring Oxygen Concentration of Biological Systems", *Oxygen Transport to Tissue VIII*, Longmuir, ed., Plenum (Aug. 1986).

Vanderkooi et al., "An Optical Method for Measurement of Dioxygen Concentration Based upon quenching of Phosphorescence", *J. Biol. Chem.* 262 (12):5476–5482 (Apr. 1987).

Wilson et al., "The Oxygen Dependence of Mitochondrial Oxidative Phosphorylation Measured by a New Optical Method for Measuring Oxygen Concentration", *J. Biol. Chem.*, 263:2712–2718 (1988).

(List continued on next page.)

*Primary Examiner*—Eric F. Winakur
(74) *Attorney, Agent, or Firm*—Evelyn H. McConathy; Dilworth Paxson LLP

(57) ABSTRACT

The invention provides an improved, reliable and efficient way of measuring the oxygen concentration gradient in a sample by a novel apparatus and accompanying method of calculating linear oxygen concentrations within the sample, permitting diagnostic testing, for example, of the effects of a developmental or metabolic change in a cell or tissue, in vitro or in vivo, in response to disease, injury radiation, or mechanical or chemical intervention, or simply to changed circumstances, or to measure the oxygen permeability of a membrane or plastic. The apparatus in a preferred embodiment comprises a core digital signal processor (DSP), having sufficient memory (RAM and ROM) to perform the necessary calculations, to control output of excitation light from a light source, and to collect phosphorescent lifetime data; and signal processors (A/D and D/A).

14 Claims, 4 Drawing Sheets

OTHER PUBLICATIONS

Robiolio et al., "Oxygen diffusion and mitochondrial respiration in neuroblastoma cells", *Am. J. Physiol.* 256 (6 Pt 1):C1207–1213 (Jun. 1989).

Wilson et al., "Effect of Hyperventilation on Oxygenation of the Brain Cortex of Neonates", *Adv. Exp. Med. Biol.* 316:341–346 (1992).

Pawlowski et al., "Monitoring of the Oxygen Pressure in the Blood of Live Animals Using the Oxygen Dependent Quenching of Phosphorescence", *Adv. Exp. Med. Biol.* 316:179–185 (1992).

Vinogradov et al., "Metallotetrabenzoporphyrins. New Phosphorescent Probes for Oxygen Measurements", *J. Chem. Soc. Perkin Trans.* 2:103–111 (1995).

Lo et al., "Calibration of Oxygen–Dependent Quenching of the Phosphorescence of Pd–meso–tetra (4–Carboxyphenyl) Porhine: A Phosphor with General Application for Measuring Oxygen Concentration in Biological Systems", *Analy. Biochem.* 236:153–160 (1996).

\* cited by examiner

APPARATUS FOR MEASURING AN OXYGEN CONCENTRATION GRADIENT AND METHOD OF USE THEREOF

This application claims the benefit of Provisional application Ser. No. 60/159,616, filed Oct. 14, 1999.

GOVERNMENT SUPPORT

This work was supported in part by grants from the National Institutes of Health, including grant numbers NS-31465, HL-60100 and CA-74052. The government may have certain rights in this invention.

FIELD OF THE INVENTION

This invention relates to methods and apparatus for measuring an oxygen concentration gradients and method of use thereof, and computer program products therefor.

BACKGROUND OF THE INVENTION

Although others have attempted to measure oxygen concentrations to provide information regarding tissues and other in vivo environments, e.g., Vanderkooi et al., *J. Biol. Chem.*, 262 (12):5476–5482 (April 1987); U.S. Pat. No. 4,476,870; U.S. Pat. No. 4,947,850; U.S. Pat. No. 5,186,173; U.S. Pat. No. 5,515,864, there has remained a need in the art for an apparatus and system that will quickly, accurately, and economically measure oxygen concentrations throughout a sample permitting calculation of the oxygen concentration gradient as a reliable and reproducible characterization or diagnostic tool.

SUMMARY OF THE INVENTION

The present inventors have responded to the need for an improved, reliable and fast way of measuring the oxygen concentration gradient in a sample by developing an novel apparatus and accompanying method of calculating linear oxygen concentrations in the sample, permitting diagnostic testing, for example, of the effects of a developmental or metabolic change in a cell or tissue, in vitro or in vivo, in response to disease, injury, radiation, or mechanical or chemical intervention, or simply to changed circumstances, or to measure the oxygen permeability of a membrane or plastic.

In accordance with one aspect of the present invention, there is provided an apparatus comprising:

- a core digital signal processor (DSP), having sufficient memory (RAM and ROM) to perform the necessary calculations, to control output of the excitation source, and to collect phosphorescent lifetime data;
- a first Delta Sigma signal processor (D/A, digital to analog) for converting tabulated calculated data to current to control an excitation light signal from the selected light source;
- an avalanche photodiode to photomultiplier for filtering and detecting emitted phosphorescent light from the sample following exposure to the excitation light signal;
- an amplifier for amplifying the output of the photodiode or photomultiplier; and
- a second Delta-Sigma signal processor (A/D analog to digital) responsive to the amplified output from the photodiode or photomultiplier, for digitizing the amplified photodetector output (the emitted phosphorescence), and for compiling collected data into a separate memory set, m (the tabulated calculated data), in the DSP, wherein data is summed to recover distribution of the phosphorescent lifetimes, from which oxygen concentration gradient is calculated from at least one equation.

In another embodiment of the invention an apparatus is provided, wherein the data collected by the second signal processor (the digitizer) is synchronized with the first signal processor (the D/A unit) to control the driving current controlling the selected light source. The preferred apparatus relies on the principle that the emitted phosphorescence is functionally related to oxygen quenching when exposed to excitation light, and that the light source introduces a plurality of signals into the sample, such that a set of signals is established in the sample, wherein a waveform is derived, and wherein all component waveforms pass through zero.

An apparatus is also provided, wherein the photodetector or photomultiplier detects a plurality or emitted signals corresponding to a plurality or excitation signals introduced into the sample as the excitation light, and wherein the detection means determines a solution of at least one equation based upon variations in the respective values of the signal parameters of the plurality of detected emission signals. In a preferred embodiment all modulation frequencies are mixed in a excitation light, the oxygen concentration gradient is extracted from a dependence of phosphorescence amplitude and phase angle on the modulation frequency in the plurality of detected signals.

An apparatus is further provided, wherein the photodetector or photomultiplier detects a plurality of emitted signals corresponding to a plurality of emitted signals (phosphorescence), wherein the frequency and amplitude of said emitted signals is inversely related to quenching by oxygen in the sample, and wherein the detection means determines a solution of at least one equation based upon variations in the respective values of the signal parameters of the plurality of detected emission signals.

The invention further provides an apparatus, wherein the detection signal processor further comprises a means for regularizing the detected phosphorescence signals; and a means, responsive to said regularizing means, for representing the regularized signals by a Maximum Entropy solution using fast, non-iterative quadratic programming algorithm at each maximizing step to interpolate a histogram representing the best underlying distribution of the phosphorescence lifetimes. In addition, the preferred apparatus further converts the histogram representing the best underlying distribution of phosphorescence lifetimes into a distribution of oxygen concentrations by the Stern-Volmer relationship.

In certain additional embodiments of the invention, the apparatus further comprises a high sensitivity video camera for measuring the emitted phosphorescence from the phosphorescent compound. One or more steps of the method or apparatus may also be automated.

Further provided, is a method for determining an oxygen concentration gradient in a sample comprising: (i) dissolving or introducing a hydrophilic phosphorescent compound in the sample, wherein quenching constant and lifetime at zero oxygen are known or previously determined for the phosphorescent compound; (ii) illuminating the sample with a pulsed or modulated excitation light at an intensity and frequency sufficient to cause the phosphorescent compound to emit a measurable phosphorescence; (iii) measuring the emitted phosphorescence; and (iv) calculating the phosphorescence lifetime and oxygen concentration gradient in the sample.

The invention also provides a computer program product for determining oxygen concentration gradient from detected phosphorescence lifetimes in a phosphor-containing sample based upon a signal that has propagated through at least a portion of the sample, wherein the signal varies with respect to excitation frequencies from an excitation light source and emitted phosphorescence, wherein the emitted phosphorescence varies in an inverse direct relationship to oxygen quenching in the sample, and wherein the computer program product comprises a computer-readable storage medium having computer-readable program code means embodied in said medium, said computer-readable program code means comprising:

a first computer-readable program code means for analyzing the emitted phosphorescence signal detected from the sample to determine variations in the signal with respect to a predetermined quenching constant and maximal lifetime at zero oxygen for the phosphor;

a second computer-readable program code means, responsive to said first computer-readable program code means, for constructing one or more equations at least partially based upon the signal, wherein an equation extracts the dependence of phosphorescence amplitude and phase angle with the summation of modulation frequencies in the excitation light;

a third computer-readable program code means, responsive to the second computer-readable program code means, for determining a solution of the one or more equations, which has been constructed to resolve the variations in phosphorescence amplitude and phase angle with respect to modulation frequencies and the quenching constant and maximal lifetime at zero oxygen for the selected phosphor;

a fourth computer-readable program code means, responsive to the third computer-readable program code means, for determining the solution of the one or more equations, wherein the fourth computer-readable program means comprises computer-readable program code means for recovering an algorithmically-determined histogram which maximally resembles the phosphorescence lifetime distribution of the selected phosphor in the sample; and a fifth computer-readable program code means, responsive to the fourth computer-readable program code means, for determining the solution of the one or more equations, wherein the fifth computer-readable program means comprises computer-readable program code means for algorithmically-converting the phosphorescence lifetime distribution into a corresponding oxygen concentration gradient based upon the Sterne-Volmer relationship.

In addition, the present invention provides methods of using the apparatus described above to detect phosphorescence lifetimes in a phosphor-containing sample, and in preferred embodiments to determine therefrom an oxygen concentration gradient in a phosphor-containing sample.

The invention will be more fully understood from the following detailed description of preferred embodiments, drawings and examples, all of which are intended to be for illustrative purposes only, and not intended in any way to limit the invention.

BRIEF DESCRIPTION OF THE DRAWINGS

The foregoing summary, as well as the following detailed description of the invention, will be better understood when read in conjunction with the appended drawings.

DETAILED DESCRIPTION OF EMBODIMENTS OF THE INVENTION

The present invention comprises an apparatus for measuring an oxygen concentration gradient in an aqueous environment and methods of calculating the resulting measurements. The present invention uses the phenomenon of oxygen dependent quenching of phosphorescence, combined with non-toxic, soluble phosphors, and provides an efficient, reliable and economical method and apparatus to quickly and quantitatively determine oxygen concentrations.

The invention is embodied by an apparatus for measuring the linear oxygen concentration in a sample comprising the following elements: a) a means for illuminating the sample, wherein the sample comprises a phosphorescent compound, at an intensity and frequency sufficient to cause the phosphorescent compound to emit a measurable phosphorescence; b) a means for measuring the emitted phosphorescence; and c) a means for calculating the phosphorescence lifetime and oxygen concentration gradient in the sample.

In a preferred embodiment, the apparatus 40 comprises a phosphorometer photodetector or device 41 for measuring emitted phosphorescence, containing a core digital signal processor (DSP) 45 with sufficient memory (RAM and ROM) to carry out the indicated calculations and to control both the output of the excitation light source and collection of the phosphorescence data. In addition, the device contains Delta-Sigma signal processors (DSP) (both A/D 44 and D/A 46) for converting calculated data tables to current for the excitation light (D/A), and for digitizing the photodetector output (A/D) for digital analysis. The DSP, A/D and D/A are preferably 16 bit or greater, and the memory is preferably able to operate in 32 bit words or greater.

Figure 4:
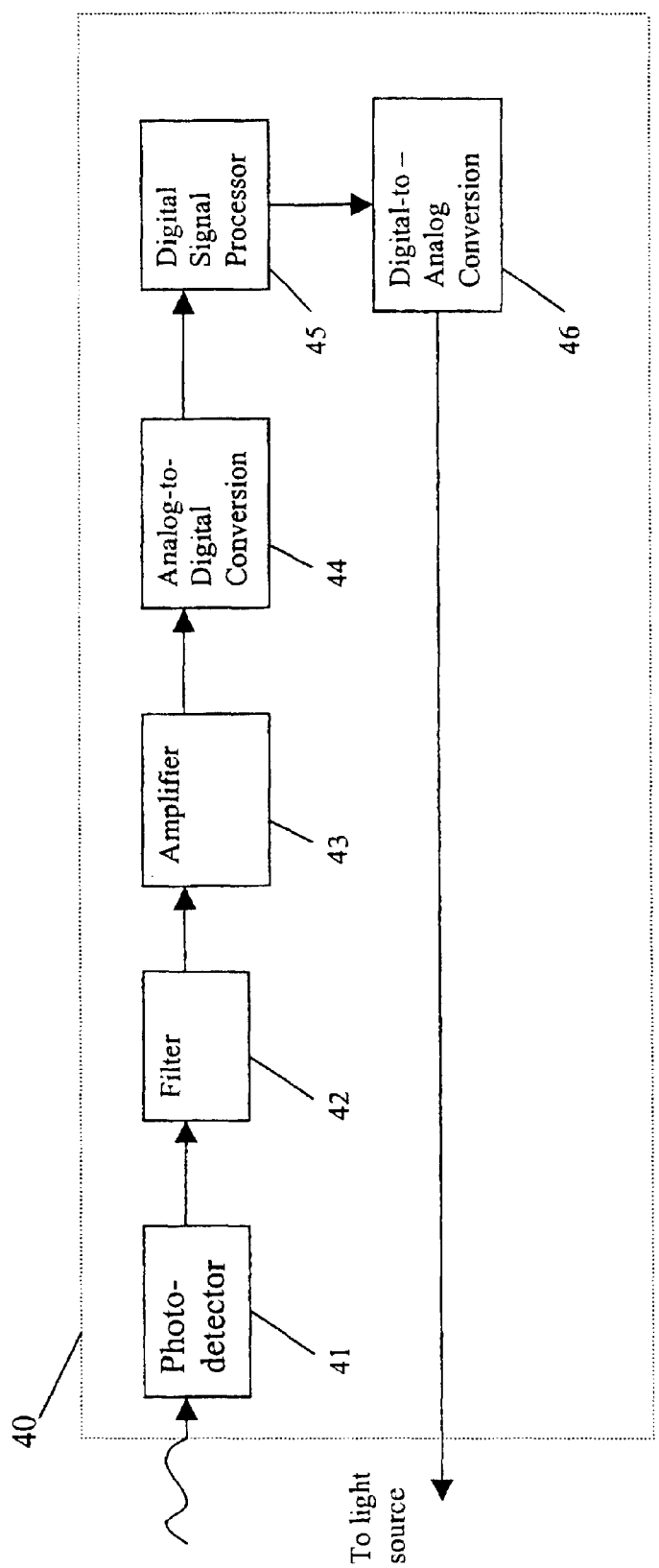
FIG. 4 is a block diagram depicting the flow of information through a preferred embodiment of the apparatus of the present invention.

A preferred instrument for the practice of the present invention is a phosphorometer, comprising a core digital signal processor which can be constructed from, for example, Analog Devices ADSP-2181 and AL 1847 Stereo Codex with stereo high precision 48 kHz, 16 bit, 20 Delta-Sigma ADCs with 64× oversampling. The instrument (as shown in FIG. 4) further comprises a filter 42, such as an avalanche photodiode or photomultiplier for filtering and detecting emitted phosphorescent light from the sample following exposure to the excitation light signal. Moreover, as shown in FIG. 4, the instrument further comprises an amplifier 43 for amplifying the output of the photodiode or photomultiplier, and a second Delta-Sigma signal processor (A/D analog to digital) responsive to the amplified output from the photodiode or photomultiplier, for digitizing the amplified photodetector output (the emitted phosphorescence), and for compiling collected data into a separate memory set, m (the tabulated calculated data), in the DSP, wherein data is summed to recover distribution of the phosphorescent lifetimes, from which oxygen concentration gradient is calculated from at least one equation.

A sine wave signal of the desired frequency can be generated by the DSP using a 16 bit DAC and smoothing circuits of the Stereo Codex. The resulting signal will control the current in the LED or laser diode driving circuit. The LED driver circuit is designed to provide a greater than 90% modulation of light output. This is accomplished by adding a DC signal to the sinusoidal signal, such that the minimum current is just above the threshold for light emission. Above this threshold, the light output is a nearly linear function of the current through the LED.

In practice, the apparatus of the present invention applies the following principles. Non-toxic phosphorescent compounds are dissolved in the sample or introduced into the sample being tested. Then, the sample is illuminated with pulsed or modulated light to raise the phosphorescent molecules to an excited state, and the resulting phosphorescent light. The decay constant is calculated from the resultant measurements; thereby permitting determination of the oxygen concentration gradient in the sample.

Phosphorescent Compounds or Phosphors

Measurements in the invention are based upon the quenching of the phosphorescence of a phosphorescent compound having a known quenching constant and known lifespan at zero oxygen for a given temperature. Repeated measurements can be used as a quantitative analysis of the time course of alterations in oxygen content in response to changed conditions. If the quenching constant and lifespan are unknown for a particular compound or phosphor, values can be determined by calibrating the quenching constant and lifetime at zero oxygen.

"Phosphors" or "phosphorescent compounds" of the present invention include any $O_2$-sensitive compound which is soluble in the substrate being tested, and which upon excitation by a selected light source will produce a measurable phosphorescent light. The phosphorescent lifetime of the phosphors suitable for the present invention is diminished or reduced ("quenched") by $O_2$. The preferred selected phosphors are hydrophilic or water soluble, and generally biocompatible.

Although not intended to be limiting, suitable phosphorescent compounds include those describe in U.S. Pat. No. 5,830,138 and co-pending U.S. Ser. No. 08/137,624, each of which is incorporated herein by reference, and as published in Vinogradov et al., *J. Chem. Soc., Perkin Trans.* 2:103–111 (1995). Preferred porphyrins of the present invention include those hydrophilic compounds having the following formula:

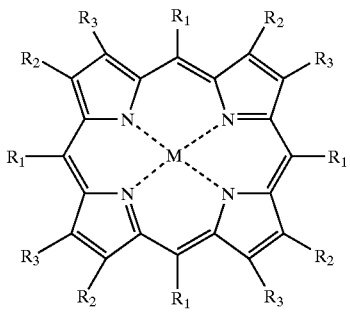

wherein $R_1$ is a hydrogen atom or a substituted or unsubstituted aryl; $R_2$ and $R_3$ are independently hydrogen or are linked together to form substituted or unsubstituted aryl; and M is a metal. In certain preferred embodiments, M is a metal selected from the group consisting of Zn, Al, Sn, Y, La, Lu, Pd, Pt and salts and derivatives thereof. Examples of such porphyrins, while not intended to be limiting, include, e.g., tetrabenzoporphyrin, tetranaphthoporphyrin, tetraanthraporphyrin, and derivatives thereof. More specifically, examples of applicable porphyrins, include, e.g., meso-tetraphenylated derivatives; tetraphenyltetrabenzoporphyrins; tetraphenyltetranaphthoporphyrins; meso-tetra-(4-carboxylphenyl) porphyrins; meso-tetraphenyltetrabenzoporphyrins; meso-10 tetraphenyltetranaphthoporphyrins; and tetrabenzoporphyrins.

More preferred for use in the present invention are known dendritic derivatives of the aforementioned porphyrin phosphors, which are highly efficient and highly soluble phosphorescent compounds surrounded by an inert globular structure. An example of such a compound is a derivatized metallotetrabenzoporphyrin compound, such as Pd-tetrabenzo-porphyrin or Pd-meso-tetra-(4-carboxyphenyl) porphyrin. As disclosed in the '138 patent, substituent groups are known to impart desirable properties, such as solubility, to the preferred phosphorescent compounds.

The preferred porphyrin structures are surrounded by a three-dimensional supramolecular structure known as a dendrimer. It is known that one-, two-, and three-layer polyglutamate dendritic cages synthesized divergently around novel derivatized extended metalloporphyrin, oxygen-measuring, phosphor compounds provide phosphors which are highly water-soluble in a wide pH range and display a narrow distribution of phosphorescence lifetimes in deoxygenated water solutions.

The phosphor-containing sample is exposed to a modulated light source capable of exciting the phosphor to emit phosphorescent light, which permits measurement and calibration of both the phosphorescence intensity and delay time between the excitation light intensity and the phosphorescence emission (signal). Therefore, accurate determination of the frequency dependence of the signal amplitude and phase is used to calculate the oxygen pressure histogram of the sample using algorithms. The measured oxygen pressure histogram can then be used to accurately calculate the oxygen concentration gradient throughout the sample.

Phosphorescence quenching has been thoroughly verified as a method of measuring the oxygen dependence of cellular respiration (see, for example, Vanderkooi, J M, and Wilson D F, "A New Method for Measuring Oxygen Concentration of Biological Systems, in *Oxygen Transport to Tissue VIII*, Longmuir, ed., Plenum (August 1986); Vanderkooi, J M, et al., *J. Biol. Chem.* 262, No. 12:5476–5482 (April 1987); Wilson et al., *J. Biol. Chem.*, 263:2712–2718 (1988); Robiolio et al., *Am. J. Physiol.* 256 (6 Pt 1):C1207–1213 (June 1989); Wilson, D F, et al., *Adv. Exp. Med. Biol.* 316:341–346 (1992); and Pawlowski, M, et al., *Adv. Exp. Med. Biol.* 316:179–185 (1992). For detailed data on the calibration techniques and oxygen measurement capabilities of one widely used phosphor, see Lo et al., Analy. Biochem. 236:153–160 (1996). At constant temperature, phosphorescence lifetime is independent of the other parameters and composition of the sample.

It is important in the present invention to use a compound of known quenching constant and known lifetime at zero oxygen for a given temperature. Thus, once the compound and temperature are determined, calibration need only be made on a single occasion, after which the value can be used for all subsequent measurements involving that compound.

Measurements according to the present invention are rapid and highly reproducible. Less than 2 seconds are required for each measurement and current instruments have a measurement-to-measurement variability of less than 1 part in 1000. Due to the absolute calibration, equally low variability is attained among different samples having the same oxygen pressure.

Excitation of the Phosphor(s)

In accordance with the invention, a light source means, preferably a modulated light source, is employed for excitation of the soluble phosphor compound in the sample to a state of phosphorescence. A beam of excitation light is passed through the sample from any direction, i.e., top to bottom, bottom to top or through the sides, so long as the beam passes completely through the sample, equally exciting the phosphor at all layers of the sample. The emitted phosphorescence is then collected from any point, so long as the phosphorescence is evenly distributed to the collection point.

Phosphorescence lifetime measurements use modulated excitation light, i.e., undulated sinusoidally, from 20 to 50,000 Hz, preferably from 50 to 35,000 Hz, most preferably from 100 to 20,000 Hz. The preferred measurements detect only those emissions that are at a longer wavelength and modulated at the same frequency.

The light source means can be provided by any of several different sources, including a flash lamp, a pulsed light emitting diode, or a pulsed laser. In the preferred mode, the light source is a light-emitting diode (LED), such as a laser diode. LEDs provide monochromatic light with a relatively broad bandwidth. The light is preferably passed through an interference filter to block the long wavelength "tail" in the emission of the LED, which might otherwise interfere with the measurements of the present invention. Solid state light sources can be readily modulated at the desired frequency and are monochromatic, i.e., light emission occurs primarily in either a broad band up to about 60 nm bandwidth at halfheight for LEDs or at a narrow band of 1 nm or less for laser diodes. As a result, minimal optical filtering is required for optimal application of such light to the measurement of phosphorescence lifetimes.

Modulation of the light can be achieved either by direct modulation of the light source or by passing the light through a modulation device, such as a flasher or a rotating wheel with slots through which the light may pass.

Measuring the Emitted Phosphorescence

The measurements of the present invention are readily adapted to very small sample sizes. The present optical method is not dependent on sample path length or light scattering. Measurements can readily be made in volumes as low as a few picoliters, and in spots with diameters of less than 20 microns.

Measurements of phosphorescence lifetime are independent of the concentration of the phosphor(s) in the medium, so long at the phosphor(s) is present in the medium at a concentration range needed for oxygen measurement. Within the functional concentration range, there is no significant "self quenching" due to energy transfer from triplet state to ground state phosphor molecules. This is because of the relatively large size and charge of the preferred dendrimer constructs. Measurements of phosphorescence lifetimes are also independent of absorption by other chromophores, such a hemoglobin, which may be present in the medium. Lifetime measurements are independent of changes in absorption and light scattering, as long as the changes do not occur during phosphorescence decay (<1 msec). This makes the method particularly effective in measuring oxygen in sample conditions affected by contaminants, such as colored components.

Based upon the principle that the beam of excitation light passed through the environment will equally excite the phosphors at all levels, and because the phosphorescence lifetime increases as the oxygen concentration in its immediate environment decreases, the calculated lifetimes are necessarily proportionally longer for points of lower oxygen concentration. Phosphorescence may be measured by any available means in accordance with the present invention.

Measuring Phosphorescent Lifetime

In general, two conventional methods for measuring phosphorescence lifetime (or decay time) are (i) the "pulse method" in the time domain, and (ii) the "phase method" in the frequency domain. The present invention is based upon applications of the phase method.

In a time domain procedure, the phosphor-containing medium (the "sensor medium") is illuminated with a short flash of excitation light and the subsequent phosphorescence decay is measured by a time domain device or instrument. In a frequency domain procedure, excitation of the sensor medium is accomplished with a modulated light source, and the phase difference between excitation and emission is measured by a frequency domain device or instrument. The measured phase difference can be deconvoluted into the distribution of phosphorescence lifetimes in the sample and the fraction of the total phosphor with each lifetime. This lifetime and volume fraction distribution can then be converted into the fraction of the sample at each oxygen pressure (concentration), thereby determining the oxygen gradient under specific test conditions.

Phosphorescence lifetime from the measured decay and/or intensity is calculated, followed by calculation of oxygen partial pressure (concentration) or gradient in the environment based upon the oxygen relationship at each point with the phosphorescence lifetime and appropriate calibration constants, i.e., quenching constant, and lifetime in the absence of oxygen. Therefore, the collected phosphorescence decay data, for example, will be the summation of the phosphorescence decays for the phosphor(s) throughout the sample.

In the pulse method, the sample is excited by a short pulse of light and the resulting phosphorescence emission in the longer wavelength is an exponentially decaying function with a measurable rate of decline. The pulse method is used in most of the existing instruments for oxygen measurement.

By comparison, in the phase method, which is the preferred method of the present invention, a sample is excited with modulated light, with absorbed light being re-emitted as phosphorescence after a certain delay period. As a result, phosphorescent emission is also modulated with the same frequency, but delayed in time (phase shifted) with respect to the excitation wave. The resulting phase shift, found experimentally, is used to calculate the phosphorescence lifetime.

The phase method is preferably used in an embodiment of the present invention because frequency lock amplification can be advantageously used to greatly increase sensitivity. Interference from ambient light is greatly decreased by this method, since only signals with the same modulation frequency as the excitation light are amplified, which largely eliminates interference by other ambient light sources.

The measurement of phosphorescence lifetimes can be fully automated, for example by using light guides or video cameras.

The values of the phosphorescence intensities and lifetimes are tabulated for later analysis, and the measurements are repeated as often as necessary until the desired endpoint is reached. The time at which the data is measured is recorded, from which the oxygen concentration can be calculated. Measurements of the phosphorescence lifetimes are extremely reproducible from instrument to instrument, due partly to the absolute calibration and partly to the nature of lifetime measurements.

Phosphorescence Detection

In practice, the phosphorescence is collected, passed through appropriate filters within or interconnected with the apparatus of the present invention. In accordance with the present invention, the phosphorometer photodetector (PD) can comprise, for example, a silicon photodiode with a built-in preamp, an avalanche photodiode, a photomultiplier, or other known PD devices such as would be known to the practitioner. The phosphorometer photodetector output is amplified to provide a signal of optimal voltage for digitizing by the analog-to-digital converter (ADC). A photodiode with an internal amplifier is selected for the optimal light sensitive surface area and lowest noise level. For example, the Hamamatsu Corporation HC120 analog photomultiplier tube assembly with an R3823 photomultiplier has an appropriate surface area (more than 5 mm$^2$) and excellent photosensitivity, in the 500 v to 900 nm wavelength range.

In a preferred embodiment of the present invention, the emitted light is filtered and detected with an avalanche photodiode. The output of the detector is amplified and passed to a 16 bit (or greater) Delta-Sigma digitizer operating at 48 or 96 kHz. The signal from the photodetector can be further amplified with an AC-coupled operational amplifier. The quality of the phase detection depends on the reduction of noise level in the photodiode output signal. After amplification, the output signal is delivered to the analog multiplexer and then input into the ADC for digitizing.

Data collection from the digitizer is synchronized with readings of the tabulated values into the D/A unit providing the driving current for the light source. Data collection is always begun at the same point in the table of values controlling the LED light output.

The digitized phosphorescence data is transferred to a specific file in memory, preferably at least a 1024×32 bit block of memory. Further data sets (a total of m data sets) are added to the same memory area, always beginning at the same point. Because the collected data are "locked" to the table of values being used to control the excitation light, only signals of exactly the same frequencies as those used to generate the excitation signal are summed positively. All other signals (and noise) are summed destructively, and their amplitudes decrease as the number of scans (m) increases. Noise amplitude, on the other hand, increases only as the square root of the number of scans summed (m$^{1/2}$), thus providing increase in signal-to-noise ratio.

In a preferred, exemplified configuration, 20 data sets would be summed. Assuming that each data set is approximately 20 msec long (1024 points at 48 kHz), summing the 20 sets would require less than 0.5 seconds.

Calculating Oxygen Distribution in Terms of Phosphorescent Lifetime

Excitation Light

The LED is modulated to provide light that is a sum of many sinusoidal waves of equal amplitude as follows:

$$Ex(t) = B + \sum_{K}^{N} A \cdot \sin(2\pi f_k t) \quad \text{(Eq. 1)}$$

The frequencies are selected such that the cycle times for the lower frequencies are multiples of the highest frequency. For example, such a set could be selected which contains 200 frequencies, spaced between 100 and 20,000 Hz, in which case, $f_k = f_j \cdot k$ when $f_j = 100$ Hz; $k=1 \ldots N$, and $N=200$.

The resulting waveform (Eq. 1) presents "nodes" or points at which all of the component waveforms pass through zero. The time between nodes is set by the lowest frequency used. These frequencies are digitally summed, and a DC offset (B, Eq. 1) is added to provide a table of values in which all values are positive. The current for driving the LEDs is obtained, for example, by sequentially reading the values in the data table into a Digital to Analog converter (preferably, 16 bits and 48 kHz) and by amplifying the signal to provide the driving current for the light source (LEDs).

Run Time Determination of Magnitude and Phase Angles for Frequencies in Array Oxygen concentration within a sample increases or decreases linearly depending upon conditions. Thus, a constant gradient is formed, which is informative of the oxygen concentration within the sample. Consequently, the oxygen concentration gradient, in combination with the diffusion constant for oxygen, can be used to accurately calculate the rate of oxygen consumption per unit area of the sample. This absolute calibration, combined with the lack of interference due to the negligible alterations in sample position, absorption, fluorescence, and light scattering, makes the present invention ideal for automated measurements.

To calculate and understand the phosphorescence lifetime distribution, and thus the oxygen distribution within the sample, the first step is to extract the dependence of the phosphorescence amplitude (a) and the phase angle (φ) on the modulation frequency.

Since all modulation frequencies are mixed in the excitation light, the emitted signal contains a spectrum of all the resulting phosphorescent lifetimes within the medium at a given point in time. Thus, following delivery of the excitation light (Eq. 1), the phosphorescence response is calculated as follows:

$$Em(t) = b + \sum_{k}^{N} a_k \sin(2\pi f_k t - \phi_k) \quad \text{(Eq. 2)}$$

where $a_k$ represents the phosphorescence amplitude and $\phi_k$ represents the phase angle for each individual frequency used in the excitation array. Therefore, by rewriting Eq. 2, using trivial trigonometry, the emitted signal is calculated as follows:

$$Em(t) = b + \sum_{k}^{N} [a_k \sin(2\pi f_k t)\cos(\phi_k) - a_k \sin(\phi_k)\cos(2\pi f_k t)] \text{ or} \quad \text{(Eq. 3)}$$

$$Em(t) = \sum_{k}^{N} [P0(f_k)\sin(2\pi f_k t) - P1(f_k)\cos(2\pi f_k t)] + P2$$

where $P0(f_k) = a_k \cos(\phi_k)$, $P1(f_k) = a_k \sin(\phi_k)$ and $P2 = b$.

In the present invention, P0(f) and P1(f) represent functions of the excitation frequency f (or frequencies $f_k$ if a frequency set was used). Using $\chi^2$-fitting ("least squares") of the phosphorescence signal, with the probe function in the form of Eq. 3, the dependencies of P0 and P1 on the modulation frequency are recovered. Alternatively, Fourier techniques can be used to obtain the dependencies. However, the disclosed calculations based upon linear algebra are, in this case, by far, more accurate, robust and fast because P0, P1 and P2 participate in the probe function (Eq. 3) as simple linear parameters.

Recovery of Oxygen Distribution in the Sample

Once the vectors (or arrays) P0($f_k$) and P1($f_k$) are obtained, they are analyzed to determine the phosphorescence lifetime distribution for the selected sample. The distribution or lifetime spectrum is directly converted into the distribution of oxygen concentrations using Stern Volmer equation.

The phosphorescence emitted at a selected time or over a time course from a sample, comprising a heterogeneous array of lifetimes, following excitation of the sample with a flash of light, is described as an integral in accordance with Eq. 4, known as the Laplace transform.

$$I(t) = \int_0^\infty g(\tau) \exp\left(-\frac{t}{\tau}\right) d\tau \qquad \text{(Eq. 4)}$$

Function $g(\tau)$ describes lifetime distribution or spectrum, while $\exp(t/\tau)$ presents what is commonly referred to as a "transform kernel." A "transform kernel" is a set of functions over which the linear integral transform is defined.

The kernel of the Laplace transform is the set of real exponential This kernel is incomplete, and so there are examples of the objects (lifetime distributions) which cannot be recovered from the Laplace images. Various numerical methods are used to invert "incomplete" integral transforms. The most probable solution for Laplace transform inversion can be obtained, for example, using the Maximum Entropy Method.

In a frequency domain the dependencies of the parameters P0 and P1 on the modulation frequency are provided by the similar integrals (Eq. 5), which are the Fourier images (sine and cosine transforms respectively) of the Laplace integral (Eq. 4):

$$P0(f) = \int_0^\infty g(\tau) \cdot \theta(f, \tau) d\tau \qquad \theta(f, \tau) = \frac{\tau}{1+\omega^2\tau^2} \qquad \text{(Eq. 5)}$$

$$P1(f) = \int_0^\infty g(\tau) \cdot \psi(f, \tau) d\tau \qquad \psi(f, \tau) = \frac{\omega\tau^2}{1+\omega^2\tau^2}$$

$$\omega = 2\pi f$$

Since the only difference between the integrals Eq. 4 and Eq. 5 are the transform kernels, while the lifetime spectrum remains unchanged, the existing algorithms for the Laplace transform inversion can be applied to the recovery of $g(\tau)$ from the data presented by P0(f) and P1(f) (Eq. 5). In such algorithms, the shape of continuous $g(\tau)$ is approximated by a finite dimension histogram. The histogram represents an array of numbers, $p=\{p_n\}$, corresponding to the fixed lifetimes $\{\tau_n\}$ (a "lifetime grid"), spanned in the range zero to ($\tau_{max}$). Maximal lifetime ($\tau_{max}$) corresponds to the phosphorescence lifetime in the absolute absence of oxygen, and thus it is the longest possible lifetime presented in the signal. The goal of the numerical methods is finding of the histogram p which maximally resembles the shape of $g(\tau)$.

Quenching of phosphorescence by oxygen is determined by the frequency of collision between the excited triplet state molecules and oxygen. This means the measured phosphorescence lifetime may be converted to oxygen pressure according to the Stern-Volmer relationship, which is stated as follows:

$$\tau_o/\tau = 1 + k_q \cdot \tau_o \cdot PO_2 \qquad \text{(Eq. 6)}$$

where $\tau_o$ and $\tau$ are the phosphorescence lifetimes in the absence of oxygen, $PO_2$ is the oxygen pressure for a lifetime of $\tau$, and $k_q$ is the quenching constant. The constant $k_q$ is related to the frequency of collisions between the excited triplet state molecules and molecular oxygen and the probability of energy transfer occurring when these molecules collide. Use of the Stern-Volmer relationship is also set forth in U.S. Pat. No. 5,501,225, which is herein incorporated by reference.

Mathematical Relationship Between Phase Shift and Phosphorescence Lifetime

In the phase approach, the mathematical relationship between phase shift and phosphorescence lifetime can be described as follows:

$$\tan\phi = 2\pi f \cdot t \qquad \text{(Eq. 7)}$$

where $\phi$=phase difference (phase shift) between excitation and emission sine waves at the modulation frequency, f, and t=lifetime of phosphorescent decay.

It can be shown that for a given signal-to-noise ratio, the lowest error in the estimation of the phosphorescence lifetime is obtained when the phase shift is about 26°.

It follows from the Stern-Volmer relationship and the diffusion equation that to maintain the phase shift of about 26° for all oxygen concentrations in the range, it is necessary to be able to vary the modulation frequencies from 20 Hz to 20,000 Hz. However, it is preferred that modulation frequencies be controlled from 100 Hz to 20,000 Hz, and instrumentation be employed which can measure phosphorescence lifetime of a given fixed frequency and/or at a first estimate optimal frequency for a given value of the phase shift (26°), and to then proceed with actual lifetime measurements. To ensure oxygen measurements are accurate to air saturation and above (lifetimes as short as <15 $\mu$sec), the phosphorescence signal is preferably sampled (digitized) at 48 kHz or greater.

The digital signals will be processed to extract the signal strength (magnitude) and phase relative to the excitation light. Calculations of the phosphorescent lifetime and oxygen pressure will follow the above-described procedures.

According to our preferred algorithm, a first approximation $p_0$ is found by applying a fast quadratic programming algorithm, based on 0-order Tikhonov's regularization. The solution is attained by maximizing a quadratic functional H(p), constructed in the following form:

$$H(p) = -\chi^2(p) - \mu(p, p) \qquad \text{(Eq. 8)}$$

where $\chi^2(p) = -(grad_0, p) + \frac{1}{2}(p, Qp)$ is a standard least squares function and $\mu(p, p)$ is a Tikhonov's 0-order smoothness regularizer. Parentheses in the expression $\mu(p, p)$, and in similar instances, denote the scalar product of the enclosed vectors, which are shown in bold. The vector $grad_0$ is an anti-gradient of $\chi^2(p)$ calculated at the origin, and Q is a Hessian matrix (matrix of the second partial derivatives of $\chi^2(p)$). For a small value of $\mu$ in the regularizer, chosen depending on the value of noise in the data, the optimization of H(p) can be effectively performed using a robust quadratic algorithm proposed by R. Shrager, *Numerical Mathematics* 15:41 (1972). This algorithm converges in the finite amount of steps and assures non-negativity of the solution $p_0$.

After the initial solution is found, the following improvement in the shape of p is achieved recursively by minimizing another functional:

$$G(p)=\chi^2(p)-\mu E(p) \quad \text{(Eq. 9)}$$

using the same algorithm and solution vector $p_i$ obtained at the previous step.

In subsequent Eq. 11, functional $E(p)=-(p, \log(p))$ refers to the Shannon-Janes entropy. The minimization of G(p) is equal to the maximization of S(p):

$$S(p)=-G(p)/\mu=E(p)-\chi^2(p)/\mu \quad \text{(Eq. 10)}$$

and, after replacing $1/\mu=\lambda$, since $\mu$ is a simple constant, Eq. 11 transforms into:

$$S(p)=E(p)-\lambda\cdot\chi^2(p) \quad \text{(Eq. 11)}$$

The value of the regularization constant is dependent on the signal to noise in the data, but is constant for computational analysis of any one data set.

The maximization of the functional S(p) is known as Maximum Entropy Method (MEM), which according to the information theory allows the recovery of the "best" uncorrelated histogram p from the noisy data.

Figure 1:
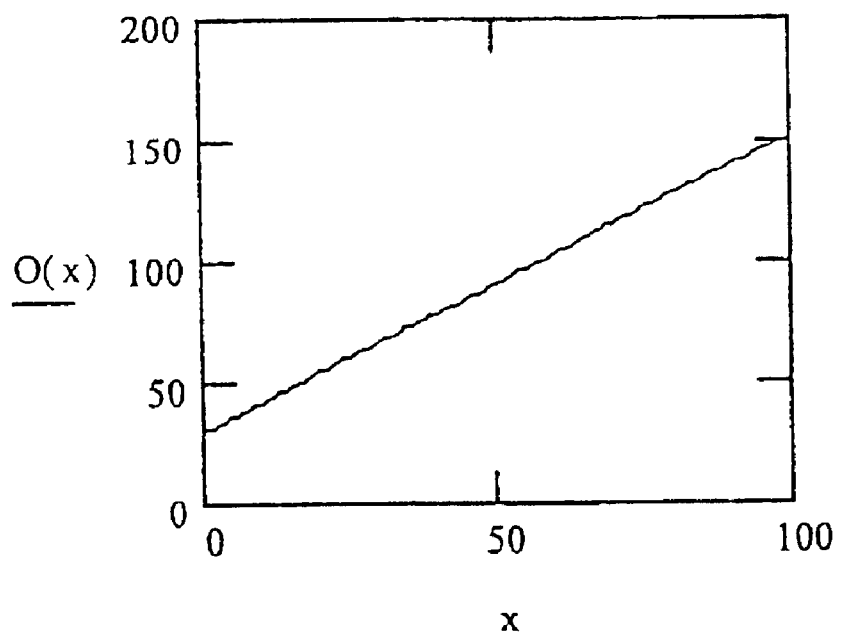
FIG. 1 is a graphical representation of an oxygen concentration gradient in a sample.
Figure 2:
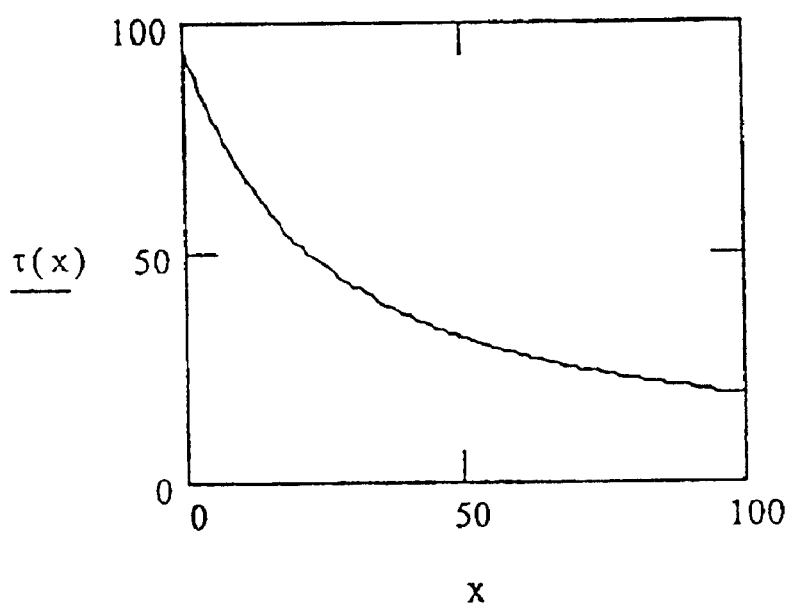
FIG. 2 is a graphical representation of phosphorescence lifetime of the phosphor in a sample.

For $O_2^{max}=152$ Torr (which is equal to the oxygen pressure in the atmosphere at sea level (20% of 760 Torr)), when $O_2^{min}=30$ Torr, and x is the selected distance within the sample (expressed in % of the total distance L), the oxygen concentration O(x) will increase as shown in FIG. 1.

Figure 3:
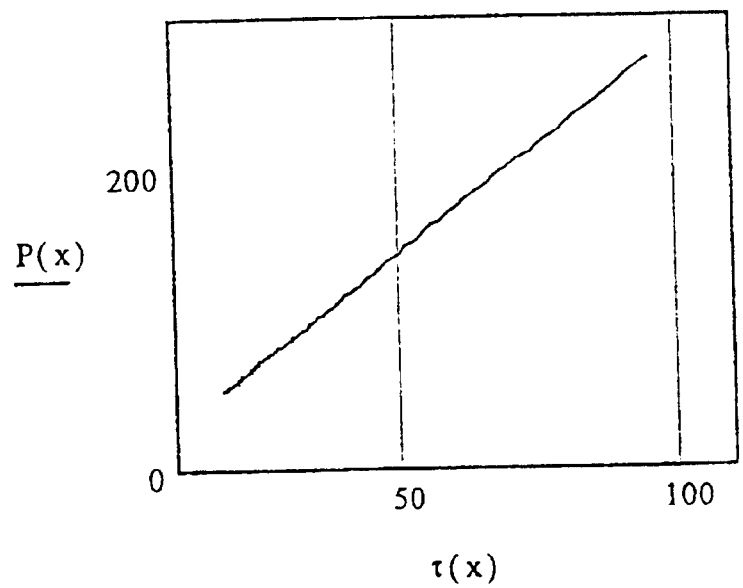
FIG. 3 is a graphical representation of intensity of phosphorescence ($P(\tau)$) versus lifetime, presenting a simple linear profile. The slope is directly related to the oxygen concentration gradient in the sample.

The phosphorescence lifetime, being the reciprocal of oxygen concentration, will hyperbolically decrease with increase of the distance x as shown in FIG. 3, which is a graph of phosphorescence lifetime versus distance within the sample. Lifetime is given in microseconds, assuming $\tau_0=350$ $\mu$sec and $K_q=350$ Torr$^{-1}$sec$^{-1}$, as characteristic for the phosphor.

However, the relative intensity $P(\tau)$ of the phosphorescence lifetime (e.g., lifetime spectrum) is proportional to the lifetime itself, and thus $P(\tau)$—the lifetime spectrum—will have a simple linear profile (FIG. 3), with the slope directly related to the oxygen gradient in the studied sample. Knowing that the distribution must have linear shape will greatly improve the accuracy and speed of the MEM recovery, as any a priory information. The information about the distribution shape can be directly incorporated into the recovery algorithm, thus permitting rapid and efficient calculation of the oxygen concentration gradients in the studied samples and providing a reliable, quantifiable and objective determination of oxygen concentrations or the effect on oxygen concentrations in a sample as a response to changed circumstances.

Each and every patent, patent application and publication that is cited in the foregoing specification is herein incorporated by reference in its entirety.

While the foregoing specification has been described with regard to certain preferred embodiments, and many details have been set forth for the purpose of illustration, it will be apparent to those skilled in the art, that without departing from the spirit and scope of the invention, the invention may be subject to various modifications and additional embodiments, and that certain of the details described herein can be varied considerably without departing from the basic principles of the invention. Such modifications and additional embodiments are also intended to fall within the scope and spirit of the invention appended claims.

We claim:

1. An apparatus for measuring the oxygen concentration gradient within a phosphor-containing sample, wherein the apparatus comprises:
    a core digital signal processor, having sufficient memory to perform the necessary calculations, to control output of the excitation source, and to collect phosphorescent lifetime data;
    a first Delta Sigma signal processor for converting tabulated calculated data to current to control an excitation light signal from the selected light source;
    an avalanche photodiode or photomultiplier for filtering and detecting emitted phosphorescent light from the sample following exposure to the excitation light signal;
    an amplifier amplifying the output of the photodiode or photomultiplier; and
    a second Delta-Sigma signal processor responsive to the amplified output from the photodiode or photomultiplier, for digitizing the amplified photodetector output, and for compiling collected data into a separate memory set, m, in the digital signal processor, wherein data is summed to recover distribution of the phosphorescent lifetimes, from which an oxygen concentration gradient is calculated from at least one differential equation.

2. The apparatus according to claim 1, wherein the data collected by the second signal processor is synchronized with the first signal processor to control the driving current controlling the selected light source.

3. The apparatus according to claim 1, wherein the emitted phosphorescence is functionally related to oxygen quenching when the sample is exposed to the excitation light.

4. An apparatus according to claim 3, wherein the light source introduces a plurality of signals into the sample, such that set of signals is established in the sample, from which set a waveform is derived, wherein said waveform all component waveforms pass through zero.

5. An apparatus according to claim 3, wherein the predetermined signal parameter is excitation frequency, and wherein said signal source introduces a plurality of signals having different respective excitation frequencies into the sample.

6. An apparatus according to claim 3, wherein the measured signal parameter is emitted phosphorescence from the phosphor-containing sample exposed to excitation light, wherein the phosphorescence is inversely related to oxygen quenching in the sample.

7. An apparatus according to claim 1, wherein the photodetector or photomultiplier further comprises a detection means which detects a plurality of emitted signals corresponding to plurality of excitation signals introduced into the sample as the excitation light, and wherein the detection means determines a solution of at least one differential equation based upon variation in the respective values of the signal parameters of the plurality of detected emission signals.

8. An apparatus according to claim 7, wherein all modulation frequencies are mixed in the excitation light.

9. An apparatus according to claim 7, wherein the oxygen concentration gradient is extracted from a dependence of phosphorescence amplitude and phase angle on the modulation frequency in the plurality of detected signals.

10. An apparatus according to claim 1, wherein the second signal processor further comprises:
   means for regularizing the detected phosphorescence signals; and
   means, responsive to said regularizing means, for representing the regularized signals by a Maximum Entropy solution using a fast, non-iterative quadratic programming algorithm at each maximizing step to interpolate a histogram representing the best underlying distribution of the phosphorescence lifetimes.

11. The apparatus according to claim 10, wherein the histogram representing the best underlying distribution of the phosphorescence lifetimes is converted into a distribution of oxygen concentrations by the Stern-Volmer relationship.

12. The apparatus according to claim 1, wherein one or more elements of the apparatus operate automatically and interconnectively.

13. A method for determining an oxygen concentration gradient in a sample comprising:
   dissolving or introducing a hydrophilic phosphorescent compound in the sample, wherein quenching constant and lifetime at zero oxygen are known or previously determined for the phosphorescent compound;
   illuminating the sample with a pulsed or modulated excitation light at an intensity and frequency sufficient to cause the phosphorescent compound to emit a measurable phosphorescence;
   measuring the emitted phosphorescence; and
   calculating the phosphorescence lifetime and oxygen concentration gradient in the sample.

14. A computer program product for determining oxygen concentration gradient from detected phosphorescence lifetimes in a phosphor-containing sample based upon a signal that has propagated through at least a portion of the sample, wherein the signal varies with respect to excitation frequencies from an excitation light source and emitted phosphorescence, and wherein the emitted phosphorescence varies in an inverse direct relationship to oxygen quenching in the sample, and wherein the computer program product comprises a computer-readable storage medium having computer-readable program code means embodied in said medium, said computer-readable program code means comprising:

first computer-readable program code means for analyzing the emitted phosphorescence signal detected from the sample to determine variations in the signal with respect to a predetermined quenching constant and maximal lifetime at zero oxygen for the phosphor;

second computer-readable program code means, responsive to said first computer-readable program code means, for constructing one or more differential equations at least partially based upon the signal which varies with respect to the predetermined constant, wherein a differential equation extracts the dependence of phosphorescence amplitude and phase angle with the summation of modulation frequencies in the excitation light;

third computer-readable program code means, responsive to the second computer-readable program code means, for determining a solution of the one or more differential equation which has been constructed to resolve the variations in phosphorescence amplitude and phase angle with respect to modulation frequencies and the quenching constant and maximal lifetime at zero oxygen for the selected phosphor;

fourth computer-readable program code means, responsive to the third computer-readable program code means, for determining the solution of the one or more differential equations, wherein the fourth computer-readable program means comprises computer-readable program code means for recovering an algorithmically-determined Maximum Entropy approximation of a histogram which maximally resembles the phosphorescence lifetime distribution of the selected phosphor in the sample; and fifth computer-readable program code means, responsive to the fourth computer-readable program code means, for determining the solution of the one or more differential equations, wherein the fifth computer-readable program means comprises computer-readable program code means for algorithmically-converting the phosphorescence lifetime distribution into a corresponding oxygen concentration gradient based upon the Sterne-Volmer relationship.

\* \* \* \* \*

UNITED STATES PATENT AND TRADEMARK OFFICE
CERTIFICATE OF CORRECTION

PATENT NO. : 6,701,168 B1
DATED : March 2, 2004
INVENTOR(S) : David F. Wilson and Sergei A. Vinogradov It is certified that error appears in the above-identified patent and that said Letters Patent is hereby corrected as shown below:

<u>Title page,</u>
Item [73], Assignee, should read -- Oxygen Enterprises, Ltd. --

Signed and Sealed this

Twenty-first Day of December, 2004

JON W. DUDAS
*Director of the United States Patent and Trademark Office*